(12) United States Patent
Kraus et al.

(10) Patent No.: US 6,434,429 B1
(45) Date of Patent: Aug. 13, 2002

(54) IMPLANT WITH CLOSE AND LONG-RANGE TELEMETRY

(75) Inventors: Michael Kraus, Forchheim; Martin Lang, Grossenseebach; Berhard Lang, Feucht; Johannes Neudecker, Erlangen; Klemens Beetz, Erlangen; Axel Nagelschmidt, Erlangen; Jens Potschadtke, Erlangen, all of (DE)

(73) Assignee: Biotronik Mess- und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/599,934

(22) Filed: Jun. 22, 2000

(30) Foreign Application Priority Data

Jun. 25, 1999 (DE) .......................... 199 30 256

(51) Int. Cl.⁷ .............................. H04B 7/00; A61N 1/08
(52) U.S. Cl. ........................ 607/60; 607/32; 128/903
(58) Field of Search .............................. 601/30–32, 60; 128/903, 904

(56) References Cited

U.S. PATENT DOCUMENTS

| | | | |
|---|---|---|---|
| 4,172,459 A | 10/1979 | Hepp | 128/697 |
| 4,173,971 A | 11/1979 | Karz | 128/702 |
| 4,531,527 A | 7/1985 | Reinhold, Jr. et al. | 128/696 |
| 4,741,341 A | 5/1988 | Marach | 128/419 |
| 4,886,064 A | * 12/1989 | Strandberg | 607/30 |
| 5,127,404 A | 7/1992 | Wyborny et al. | 128/419 |
| 5,139,028 A | 8/1992 | Steinhaus et al. | 128/697 |
| 5,197,480 A | 3/1993 | Gebhardt | 128/697 |
| 5,246,008 A | 9/1993 | Mueller | 128/695 |
| 5,292,343 A | 3/1994 | Blanchette et al. | 607/32 |
| 5,313,953 A | 5/1994 | Yomtov et al. | 128/696 |
| 5,348,008 A | 9/1994 | Bornn et al. | 128/642 |
| 5,411,031 A | 5/1995 | Yomtov | 128/706 |
| 5,411,536 A | 5/1995 | Armstrong | 607/32 |
| 5,413,594 A | 5/1995 | Williams | 607/32 |

(List continued on next page.)

FOREIGN PATENT DOCUMENTS

| | | |
|---|---|---|
| DE | 28 37 411 | 3/1979 |
| DE | 31 39 452 | 9/1982 |
| DE | 39 36 547 | 5/1991 |
| DE | 43 41 903 | 6/1995 |
| DE | 44 41 907 | 6/1995 |
| DE | 689 22 362 | 8/1995 |
| DE | 196 26 385 | 3/1997 |
| DE | 196 22 154 | 5/1997 |
| DE | 690 31 985 | 7/1998 |
| DE | 197 44 989 | 4/1999 |
| EP | 0 097 264 | 1/1984 |
| EP | 0 340 293 | 11/1989 |
| EP | 0 344 770 | 12/1989 |
| EP | 0 362 611 | 4/1990 |
| EP | 0 450 341 | 10/1991 |

(List continued on next page.)

*Primary Examiner*—Kennedy Schaetzle
*Assistant Examiner*—Kristen Droesch
(74) *Attorney, Agent, or Firm*—Christie, Parker & Hale, LLP

(57) ABSTRACT

An electromedical implant (1), in particular a cardiac pacemaker, having a close-range telemetry device for data exchange with an external apparatus (2), which includes at least a close-range antenna (47) and a close-range transmitter/receiver unit with a close-range transmitter (44), a telemetry unit (45) connected thereto and an antenna interface device (46) which is connected to the telemetry unit (45) and by way of which the close-range antenna (47) is connected to the close-range transmitter/receiver unit, wherein there is provided a long-range transmitter (48) connected to the telemetry unit (45) to provide a long-range telemetry device.

26 Claims, 10 Drawing Sheets

U.S. PATENT DOCUMENTS

Figure 1:
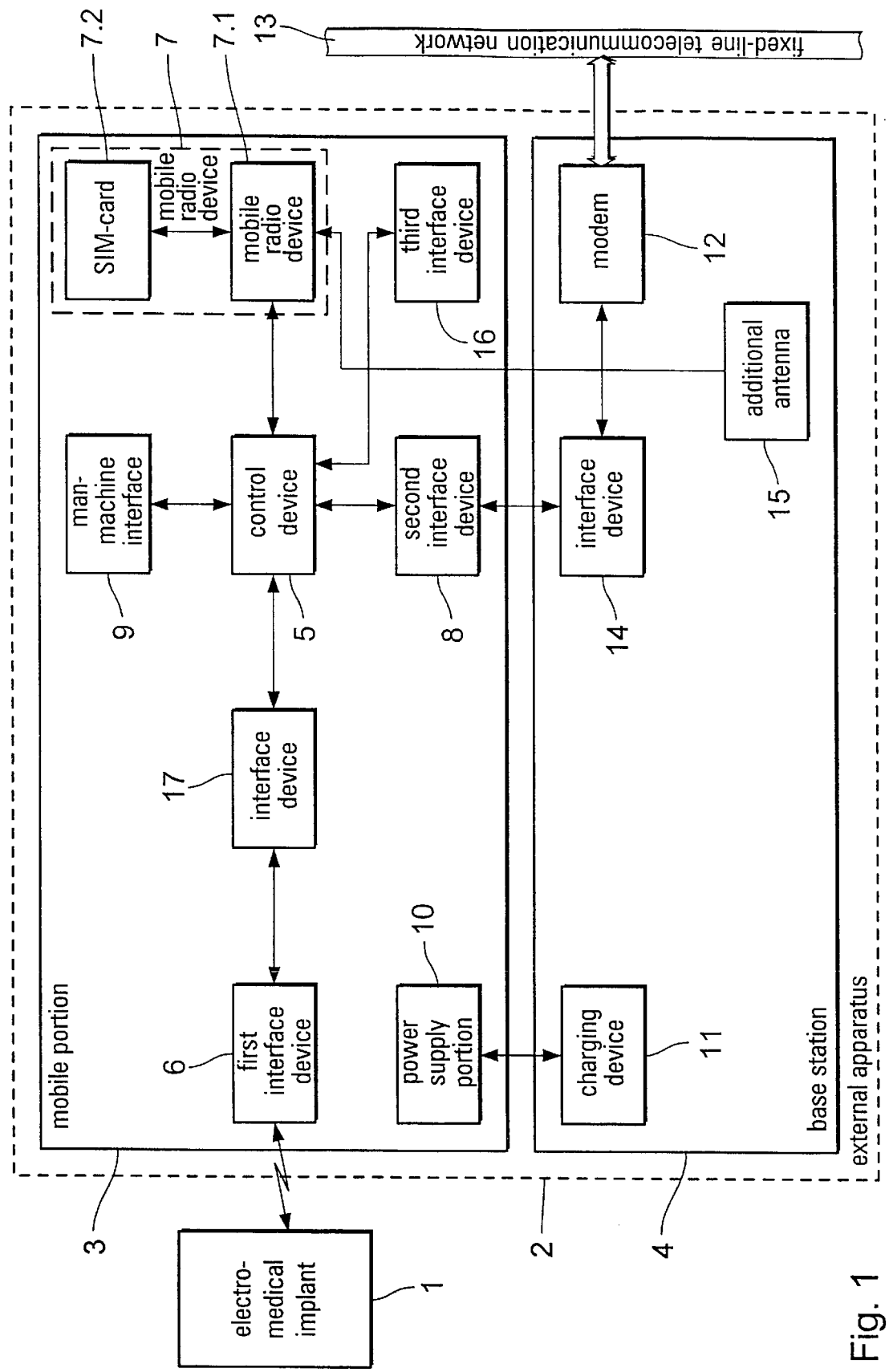

| | | | |
|---|---|---|---|
| 5,522,396 A | | 6/1996 | Langer et al. ............... 128/696 |
| 5,549,113 A | * | 8/1996 | Halleck et al. ................ 607/60 |
| 5,562,713 A | | 10/1996 | Silvian ........................ 607/32 |
| 5,626,630 A | | 5/1997 | Markowitz et al. ........... 607/60 |
| 5,720,770 A | | 2/1998 | Nappholz et al. ............. 607/30 |
| 5,729,203 A | | 3/1998 | Oka et al. ................... 340/573 |
| 5,735,887 A | | 4/1998 | Barreras, Sr. et al. ........ 607/60 |
| 5,752,976 A | | 5/1998 | Duffin et al. ................. 607/32 |
| 5,814,089 A | | 9/1998 | Stokes et al. ................. 607/32 |
| 5,999,857 A | | 12/1999 | Weijand et al. ............... 607/60 |

FOREIGN PATENT DOCUMENTS

| | | |
|---|---|---|
| EP | 0 537 936 | 4/1993 |
| EP | 0 607 638 | 7/1994 |
| EP | 0 516 617 | 1/1998 |
| EP | 0 856 333 | 8/1998 |
| JP | 07234982 | 9/1995 |
| WO | WO 97/00708 | 1/1997 |
| WO | WO 98/08567 | 3/1998 |
| WO | WO 98/42407 | 10/1998 |

* cited by examiner

IMPLANT WITH CLOSE AND LONG-RANGE TELEMETRY

The invention concerns an electromedical implant as set forth in the classifying portion of claim 1.

Known electromedical implants, for example cardiac pacemakers, defibrillators, cardioverters or other electronically actuated or controlled implants generally have a close-range telemetry device for the exchange of data with an external apparatus. Close-range telemetry is usually employed in relation to after-care examinations of a patient in a clinic or a medical practice. In this case the external apparatus is applied for data transmission to the body of the patient in the proximity of the implant.

The close-range telemetry device usually includes a close-range antenna and a close-range transmitter/receiver unit with a close-range transmitter, a telemetry unit connected thereto and an antenna interface device which is connected to the telemetry unit and by way of which the close-range antenna is connected to the close-range transmitter/receiver unit.

Other known electromedical implants have a long-range telemetry device for data exchange with an external apparatus. In this case, instead of the close-range transmitter/receiver unit, they use a long-range transmitter/receiver unit which operates in the high-frequency range and which enjoys a greater range than the close-range transmitter/receiver unit. That means that there is no need for the external apparatus to be fitted to the body of the patient. It only has to be within the range of the long-range transmitter/receiver unit of the implant.

Close-range telemetry involves the disadvantage that interrogation of the implant is possible only in the immediate proximity of a programmer or a monitoring station, whereby the mobility of the patient is under some circumstances severely limited. In comparison, long-range telemetry entails the disadvantage that, although patient mobility is increased, a relatively large amount of energy is consumed, which is disadvantageous having regard to the limited energy supplies of such an implant.

In order to minimize the disadvantages involved, it would therefore be desirable to provide an implant with both telemetry variants. In this case however the problem which arises is that naturally only a relatively limited amount of structural space is available for such implants so that it is not readily possible for both telemetry devices to be integrated in the same implant.

Therefore the object of the present invention is to provide an electromedical implant of the kind set forth in the opening part of this specification, which permits simple integration of long-range and close-range telemetry.

Based on an electromedical implant as set forth in the classifying portion of claim 1, that object is attained by the features recited in the characterizing portion of claim 1.

The invention includes the technical teaching that integration of long-range telemetry in a fashion which does not give rise to problems and which does not involve a great deal of complication and expense in an implant of the general kind set forth, with close-range telemetry, is achieved if the circuitry expenditure for long-range telemetry is minimized by virtue of using the existing circuits for close-range telemetry. For that purpose it is proposed that, to provide a long-range telemetry device, there is additionally provided a long-range transmitter connected to the telemetry unit, while the other components of the close-range telemetry device are also used for long-range telemetry. That advantageously saves not only on structural space but also manufacturing cost.

Preferably, there is provided at least one long-range antenna which is connected to the antenna interface device, as the required antennae can be of a particularly simple structure while involving the need for a small amount of space and enjoying properties which are optimized in relation to the respective kind of telemetry involved.

Close-range and long-range antennae can remain connected in parallel with each other in operation as generally the two telemetry procedures are not in any case implemented simultaneously. It is preferably provided however that, for switching over between close-range and long-range telemetry, the close-range antenna and the long-range antenna are respectively connected to the antenna interface device by way of a switching unit.

The two telemetry procedures can be operated with the same modulation method. In preferred variants however it is also possible to apply different modulation methods, in which case there is provided a matching logic circuit which is connected to the telemetry unit, for adaptation of the modulation method for the respective telemetry involved.

In preferred embodiments of the implant according to the invention the long-range telemetry device is designed for operation at substantially the same effective data rate as the close-range telemetry device, thereby avoiding additional intermediate storage means.

In order to achieve adaptation in the simplest possible manner to the different demands of the two telemetry methods, a separate energy supply is preferably respectively provided for each of the long-range telemetry device and the close-range telemetry device.

Figure 2:
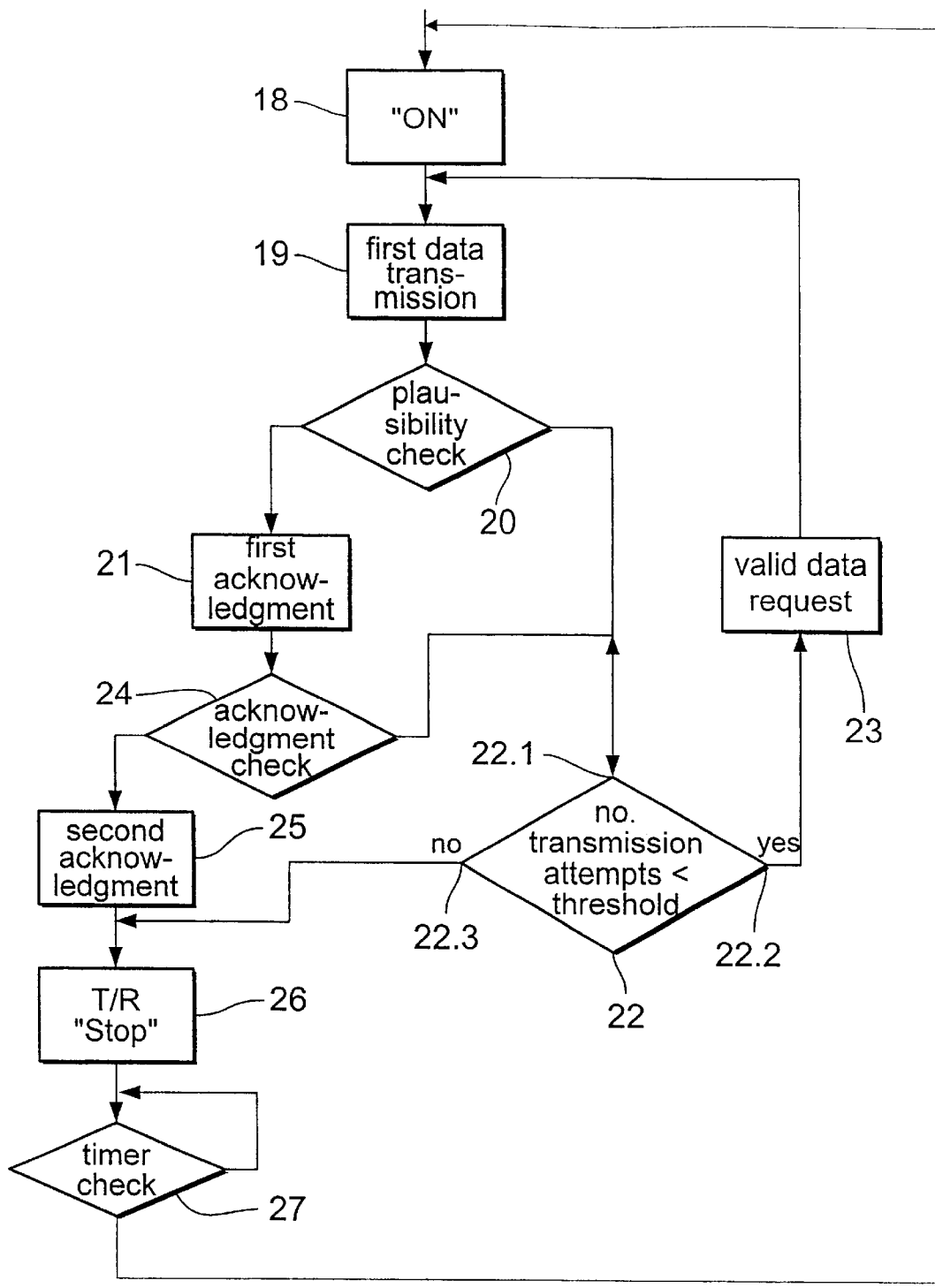
Figure 3:
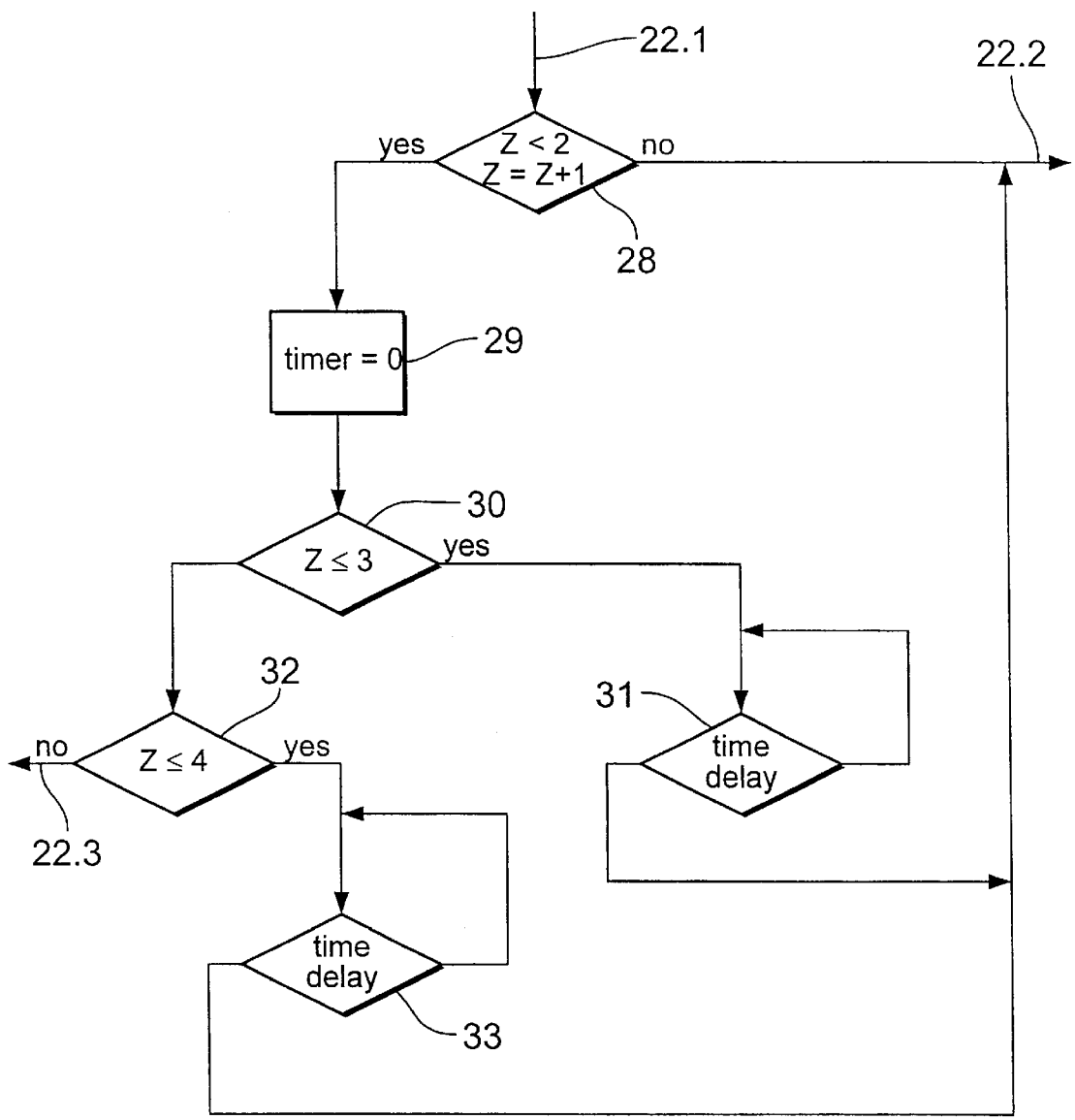
Figure 4:
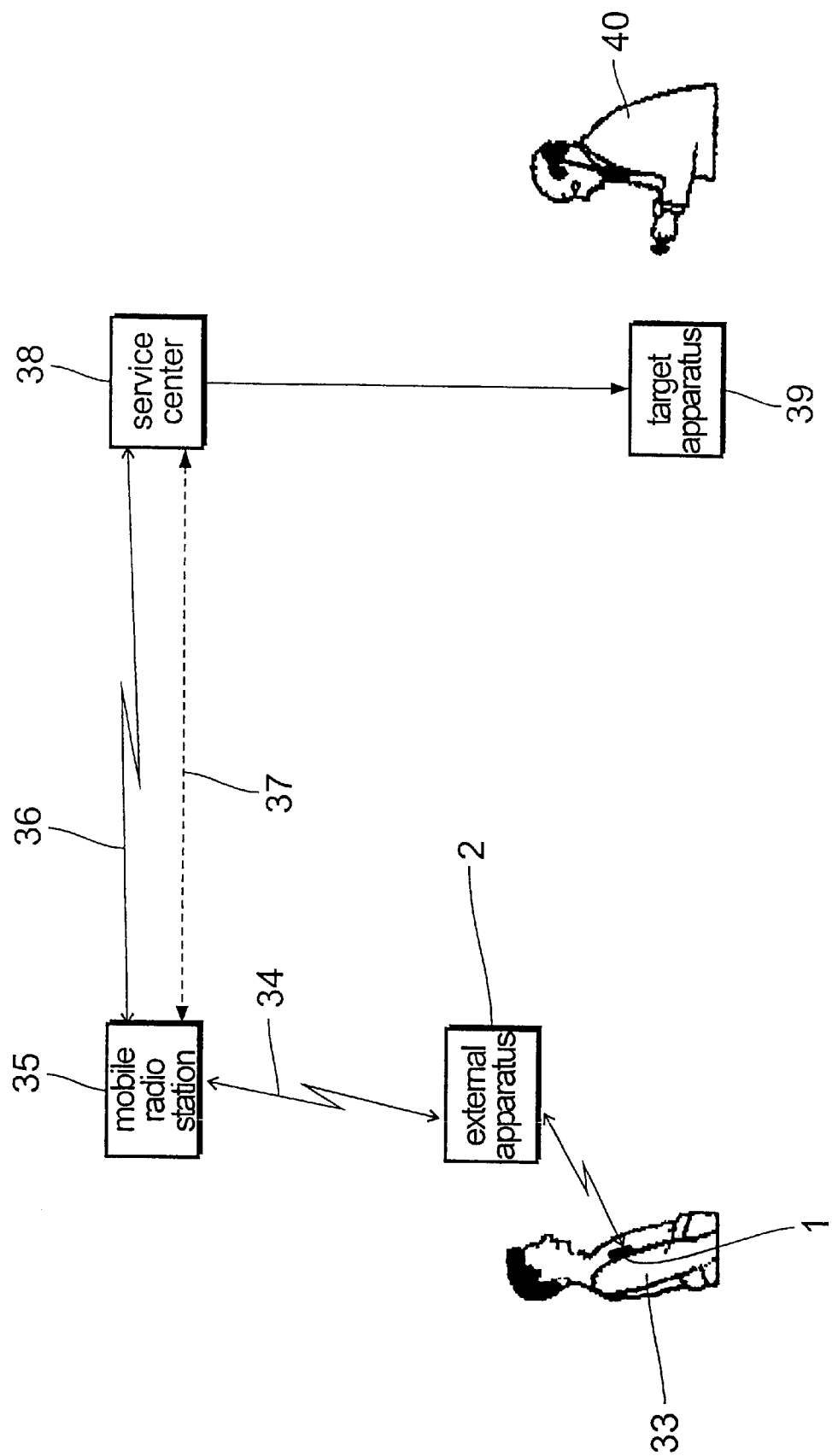
Figure 5:
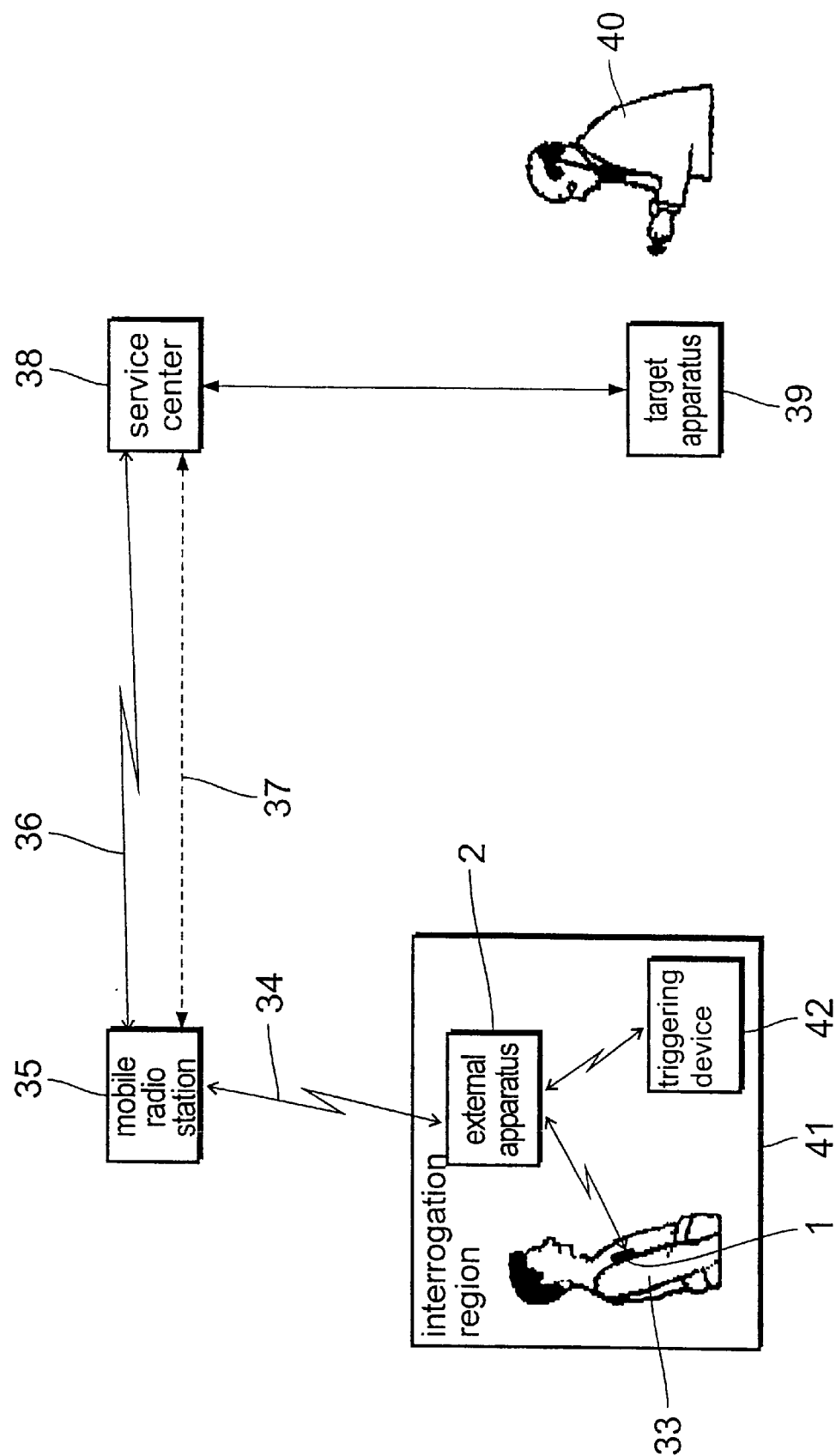
Figure 6:
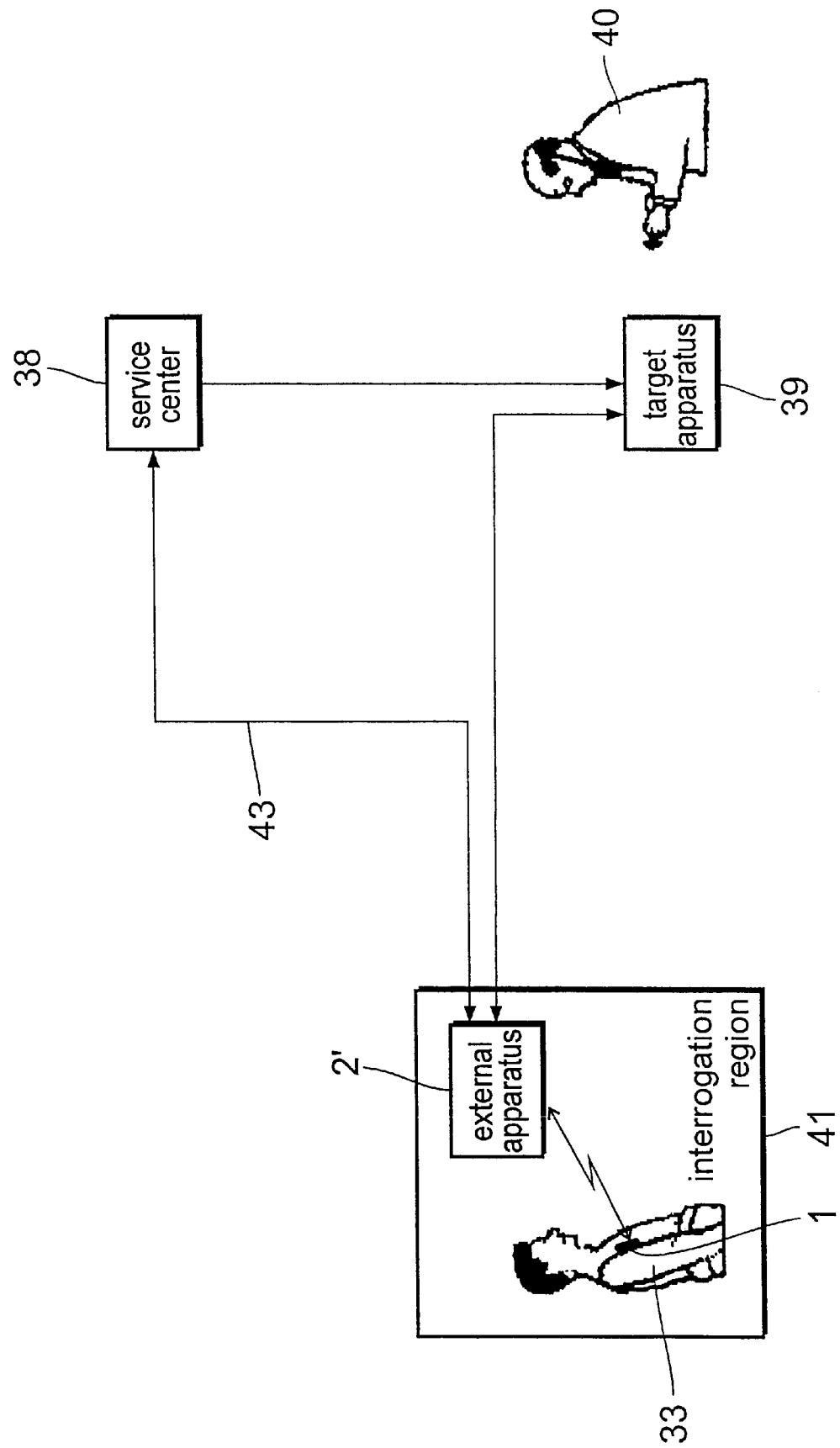
Figure 7:
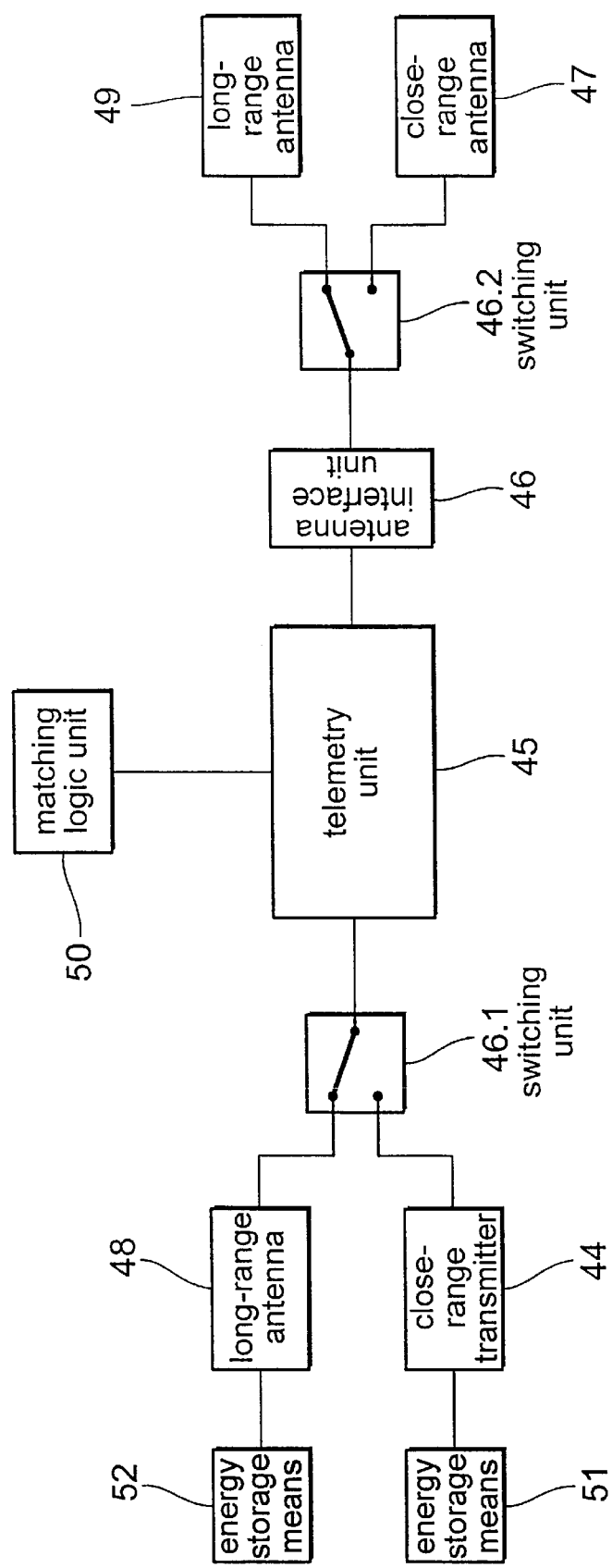
Figure 8:
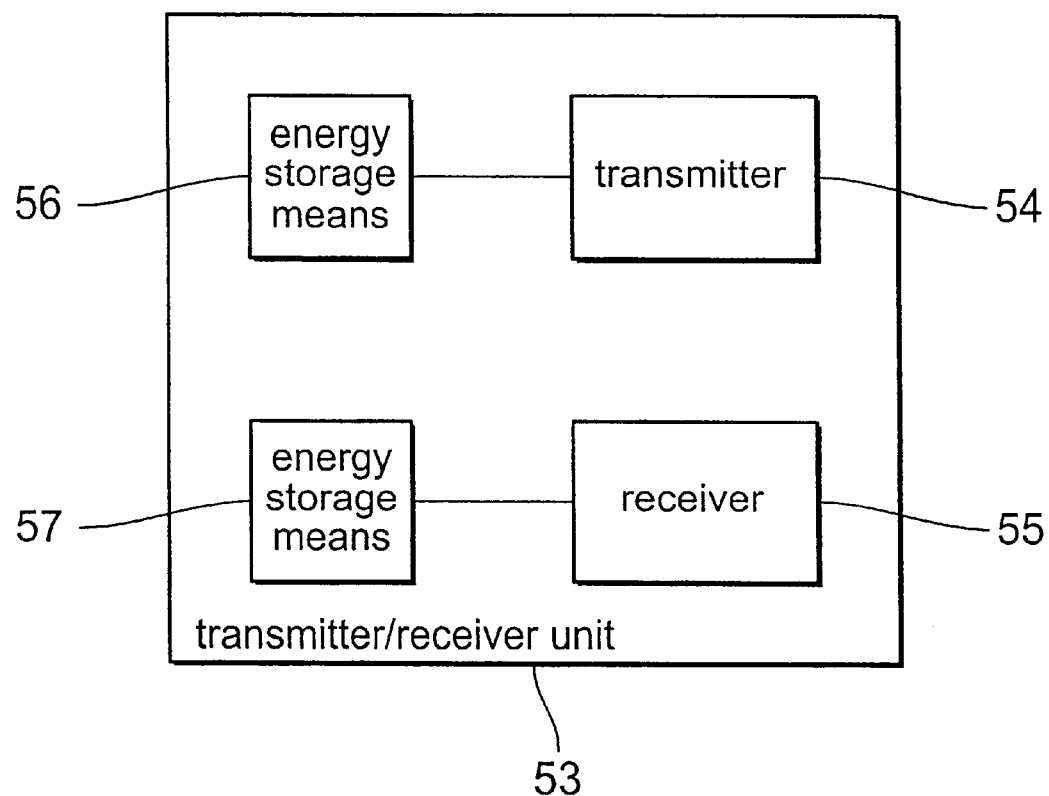
Figure 9:
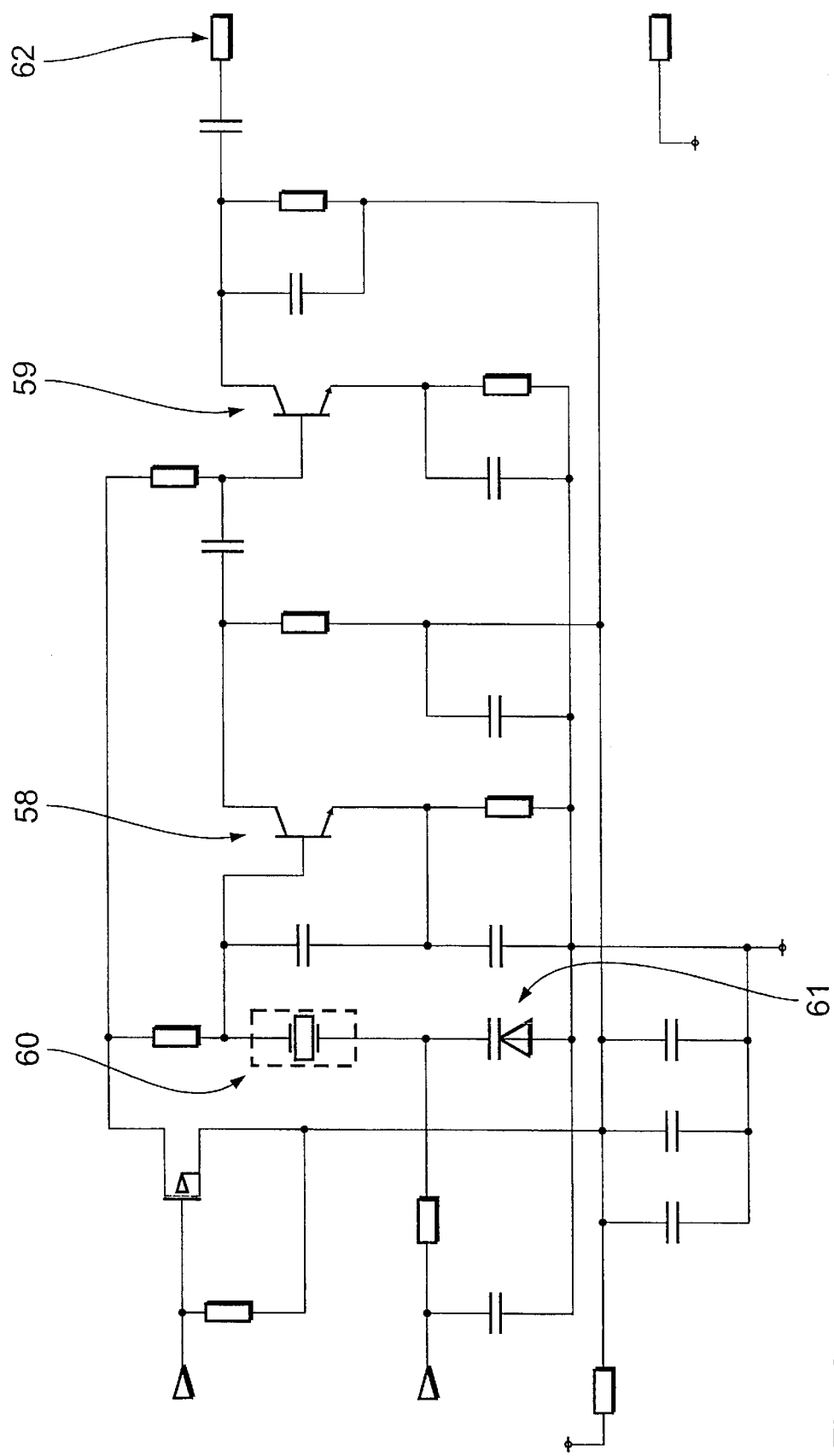
Figure 10:
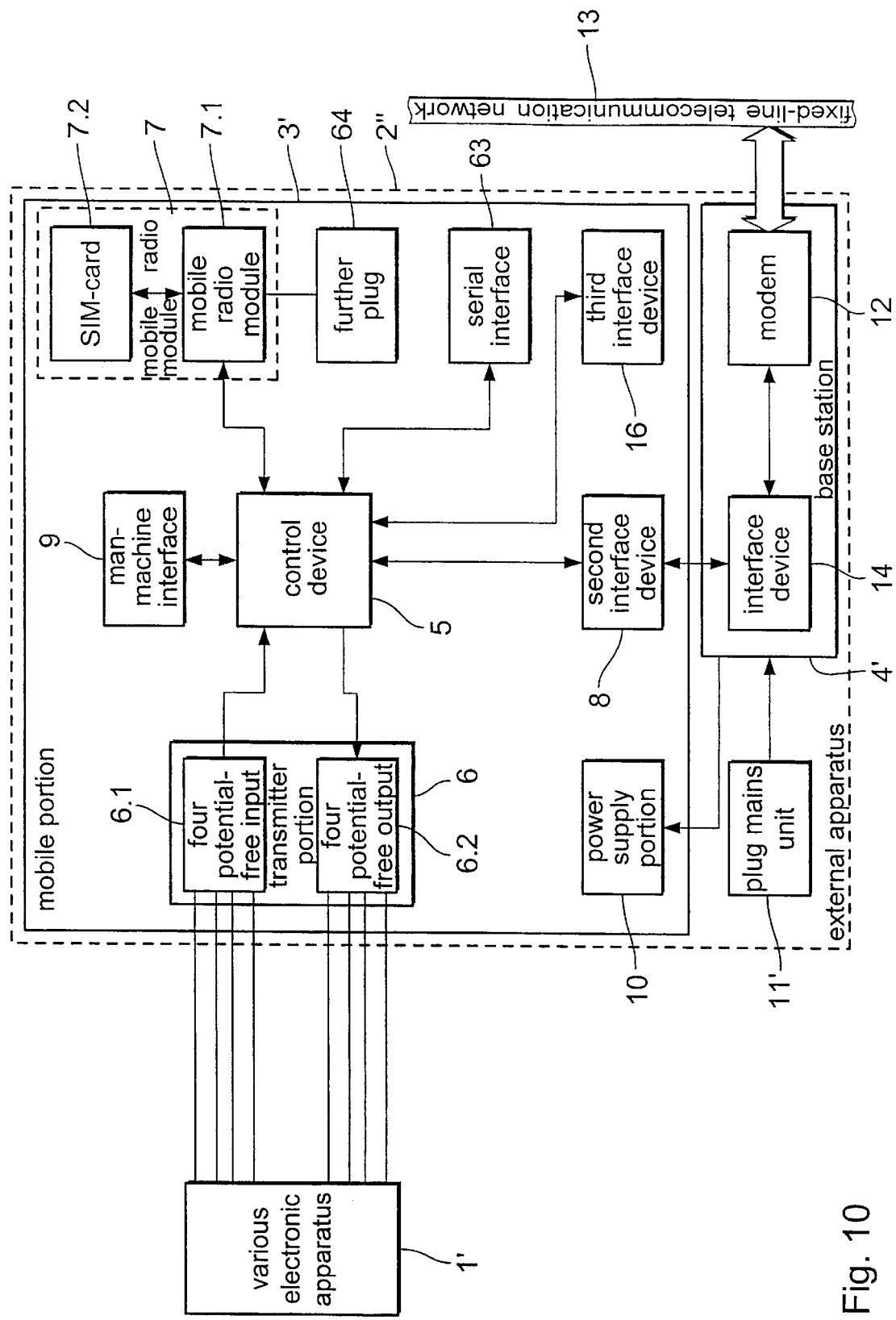

Other advantageous developments of the invention are characterized in the appendant claims and are described in greater detail hereinafter together with the description of the preferred embodiment of the invention, with reference to the accompanying drawings in which:

FIG. 1 shows a block circuit diagram of a preferred embodiment of an apparatus for carrying out the method according to the invention, FIG. 2 shows a flow chart of a method, FIG. 3 shows a detail from FIG. 2, FIG. 4 shows a block circuit diagram of a variant of a patient monitoring system using the present invention, FIG. 5 shows a block circuit diagram of a variant of a patient monitoring and after-care system using the present invention, FIG. 6 shows a block circuit diagram of a further variant of a patient monitoring and after-care system using the present invention, FIG. 7 shows a block circuit diagram of a telemetry device of an electromedical implant using the present invention, FIG. 8 shows the transmitter/receiver unit of a variant of the embodiment shown in FIG. 1, FIG. 9 shows a circuit diagram of a transmitter of a variant of the embodiment of FIG. 1, and FIG. 10 shows a block circuit diagram of a further preferred embodiment of an apparatus according to the invention.

FIG. 1 shows an apparatus for carrying out the method according to the invention with an electromedical implant 1 which is provided with a telemetry device and an external apparatus 2 which comprises a mobile portion 3 and a base station 4.

Mobile Portion 3

In this arrangement the mobile portion 3 has a control device 5 and a first interface device 6, a mobile radio device 7, a second interface device 8, a man-machine interface 9 and a third interface device 16 which are respectively connected to the control device 5. The first interface device 6 is connected to the control device 5 indirectly by way of a further interface device 17. The power supply for the mobile portion is afforded by way of Li-ion batteries which are disposed in the power supply portion 10.

The first interface device 6 comprises a telemetry transmitter/receiver unit so that the mobile portion 3 can make contact with the implant by way of a bidirectional telemetry section. The receiver and the transmitter of the interface device 6 are integrated in an IC. The two circuit portions form a functional unit. The receiver and the transmitter preferably operate in the UHF-range at 403.55 MHz, while the baud rate stages are 4, 8, 16 and 32 Kbit/s. It is however also possible to use in particular for the implant energy-saving frequencies in the VHF- or LF-range.

The mobile radio device 7 can transmit data which are read out of the implant for example by way of the first interface device 6 in the form of SMS-messages and can be called by a service center serving as a monitoring arrangement or a central storage arrangement.

A connection can be made between the mobile portion 3 and the base station 4 by way of the second interface device 8. It is in the form of an infrared interface (IrDA). It operates bidirectionally and can transmit data in the half-duplex mode.

The man-machine interface 9 makes it possible for the mobile portion 3 to be operated by a user.

The third interface device 16 is used for receiving external data or for service. It is also in the form of an IrDA interface.

The serial interface for both IrDA interface devices 8 and 16 and the interface to the mobile radio device 7 are disposed in parallel so that there is only ever one unit which can be operated. The IrDA interfaces 8 and 16 are connected in parallel. Both interfaces are continuously ready for reception so that an external request can be serviced at any time. The software then only has to establish at which IrDA interface the reception request occurs.

The power supply for the mobile portion 3 is implemented by means of Li-ion batteries. They can supply the mobile portion 3 in the fully charged-up state for at least 20 hours (standby time +16 SMS-transmissions). The dimensioning of the batteries applies in regard to the end of the operating life. The arrangement therefore has a 1000 mAh Li-ion battery.

Mobile Portion 3: Modular Embodiment

In a further embodiment which is not specifically illustrated the telemetry unit 6 for communication with the implant 1 including a transmitting/receiving antenna and an electronic actuating system for telemetry as well as an interface device 17 is disposed in a separate module. That separate module has an interface device 17 for electrical and possibly also mechanical connection to a mobile telephone.

The separate module can be fitted for example instead of the battery pack into the mobile telephone, thus affording a mechanically sturdy unit comprising the mobile telephone and a separate housing which possibly projects to an immaterial degree beyond the previous external contour of the mobile telephone.

In this variant the separate module has a battery compartment into which can be fitted the original battery pack of the mobile telephone or however another suitable battery or a suitable battery pack. That battery then serves for the power supply for the entire system consisting of the mobile telephone and the separate module and can be charged by way of the standard charging connections on the mobile telephone.

In the case of this variant, there are three basic possible options in regard to data connection between the separate module and the mobile telephone:

1 by way of the external electromechanical plug of the (usually serial) interface provided on the mobile telephone,
2 by way of an electromechanical plug of the (serial) interface provided on the mobile telephone, which plug is additionally to be integrated in the battery compartment of the mobile telephone, or
3 by way of the IrDA interface provided on the mobile telephone.

In the case of the first and third variants, there is an optical or mechanical connection between the separate module and the interface integrated in the mobile telephone, that is to say the separate module or a fixed extension thereof covers over the interface of the mobile telephone and at that location includes a suitable plug connection or extends into the proximity of the interface of the mobile telephone and includes at that end an infrared interface. Those solutions involve special software for the mobile telephone, which permits control which is initiated by way of that interface.

For integration of the plug in the battery compartment the second variant additionally requires a mechanical and electrical modification to the mobile telephone. A suitable connection of that plug not only to the serial interface but also to other parts of the electronics of the mobile telephone mean that it is possible to provide for direct control of the mobile telephone by the telemetry unit.

In both cases the known normal function of the mobile telephone is retained. Priority control for telemetry transmissions can possibly be provided. Preferably, the electronics of the mobile telephone are automatically set in operation when required by the telemetry unit which is permanently in a state of reception readiness or which is selectively time-controlled (event control).

In a further variant the separate module can be integrated on a SIM-card. That SIM-module is fitted in place of the standard SIM-card into the SIM-card tray and uses the interface provided for same as the standard.

Possibly for example the transmitting/receiving antenna and the electronic actuating system for telemetry can be so designed that, when the SIM-module is inserted, they are disposed outside the housing of the mobile telephone.

In this variant, a buzzer which is usual in mobile telephones can be actuated for acoustic display of the various patient alarm functions. The optical display which is provided in any case on mobile telephones can be used for the optical display, in all modular variants.

Mobile Portion 3: Man-machine Interface

Provided on the mobile portion 3 are a LED and a buzzer for optical and acoustic display of functions and operating states, as well as some switches for manually triggering functions.

A flashing light-emitting diode indicates the low battery state as soon as the battery charge has fallen to 10%. The mobile portion 3 then still has a minimum running reserve of about 2 hours. As the mobile portion 3 is not always visible to the patient, the buzzer, by a short alarm, also indicates the occurrence of the low battery state. The buzzer must operate at a frequency of about 2 kHz or below and must be suitably loud so that even patients of limited perception can be certain to hear the alarm sound. The buzzer should trigger an alarm again approximately every 5 minutes to remind the patient to charge up the battery.

There is provided a recessed on/off switch which cannot be unintentionally operated. The switch position is labeled so that it is possible to see whether the mobile portion 3 is switched on. That switch is necessary as the mobile portion 3 with the mobile radio device 7 must be switched off in some areas in which it is to be found, for example in an in-flight situation and in certain areas of hospitals.

There may be provided a key for sending a short message for testing the SMS-channel to the service center. The mobile portion 3 shows by means of a flashing LED that such a test has been started. The service center recognizes the received short message as being a test and sends an acknowledgment to the mobile portion 3. Flashing of the LED is thereupon terminated again, whereby the patient can see that both the outgoing and also the incoming connection to the service center are operable.

For diagnostic purposes, there can be provided a key by means of which the patient can trigger data transmissions to the service center. If the patient suffers from complaints or troubles of any kind which possibly cannot be in any way detected as such for the implant, that key can be pressed. Thereupon a data set is transmitted, which besides the items of information which are to be transmitted as a routine matter, includes the time of triggering and acquisition of the associated data by the implant. The transmitted short message also informs the service center that this is a patient-triggered data transmission which is possibly to be dealt with separately.

For acute emergency cases, it is possible to use a patient alarm key which is also protected from unintentional incorrect operation. That emergency key can be arranged in recessed relationship for that purpose and can be additionally protected by a cover which first has to be opened in order to trigger off the patient alarm. The protection against incorrect operation can also be in the form of a time lock in the software, which assumes the key function to be valid only if the key is depressed for a relatively long period of time (for example more than 3 seconds). A successfully triggered patient alarm is acknowledged acoustically by the buzzer. Thereafter the key can be released again. In addition a light-emitting diode is continuously switched on for 10 seconds and then lights up once again for 2 seconds each minute as a reminder that a patient alarm has been triggered. The buzzer is always actuated simultaneously with the light-emitting diode so that even patients of limited perception can perceive this acknowledgment from the external apparatus.

A patient alarm is immediately transmitted to the service center by way of SMS. It is canceled only when the service center acknowledges the patient alarm—also by way of SMS—, thereby ensuring that the alarm has reached the service center. Acknowledgment of the alarm by the service center is also displayed by a light-emitting diode and a buzzer on the mobile portion 3. Those measures contribute on the one hand to calming the patient, while on the other hand ensuring that, upon triggering of a patient alarm in a dangerous condition for the patient, further measures do not fail to be implemented if the patient alarm could not be transmitted successfully.

If a patient alarm which has not been acknowledged is to be canceled, the mobile portion 3 has to be switched off. After the restart the mobile portion is in the normal state again. The mobile portion automatically signals back to the service center by way of SMS. In the service center, it can then be recognized that the external apparatus was reset and the patient alarm canceled.

Successful implementation of a patient alarm situation has a higher priority in comparison with the low battery display. The low battery display is only implemented again when the service center has acknowledged the patient alarm. The mobile portion 3 is to be switched off if disturbance to the surrounding area by the buzzer is to be prevented.

Mobile Portion 3: Data Encryption

Only one processor which performs both the tasks of the central unit and also those of the communication unit is used as the control unit (or processor) 5 for the mobile portion 3. The software can be downloaded by way of the IrDA interface 16 into a flash-ROM. The memory capacity of the internal flash-ROM is 128 KBytes, that of the integrated EEPROM is 4 KBytes and that of the static external SRAM is 64 KBytes. The program memory size is thus limited to the capacity of the installed flash-ROM and cannot be expanded (Harvard structure). The external static SRAM can be expanded.

SMS-transmission is implemented using a 128 bit DES encryption process which is based on a private-public key system. Encryption is implemented in software terms, that is to say no encryption IC is used. For safe operation, the system uses a watchdog circuit which at regular intervals checks the processor 5 and puts it into a secure status again if program execution is not taking place correctly.

No further encryption is required on the way from the implant 1 to the external apparatus 2 because of the short range in addition to the implant-specific encoding of the data.

Mobile Portion 3: Position-finding

It is provided for the mobile radio device 7 that the field strength information with the associated numbers of the current and adjoined cells and the bit error rate is transmitted by way of SMS. On the basis of that position-finding information it is possible to locate the mobile portion 3 in emergency situations in which the patient is incapacitated.

Mobile Portion 3: Call Number Management

The mobile radio device 7 includes a mobile radio module 7.1 and a memory in the form of a SIM(Subscriber Identity Module)-card 7.2. The SIM-card reader can be soldered directly into the circuit board under the mobile radio module 7.1. The SIM-card 7.2 is thus not accessible to the user. A SIM-card reader is provided in any case in embodiments which are based on the use of a mobile telephone.

The call number or numbers of the service center is or are permanently stored in the memory of the SIM-card 7.2 by the mobile radio module 7.1. The mobile portion 3 is supplied with a SIM-card which contains the call number of a service center in the call number memory as a preset parameter. The call numbers on the SIM-card can be altered by way of SMS. Call number management (writing and reading the numbers on and from the SIM-card) must be implemented by the central control device 5 of the external apparatus. The preset call number is kept permanently on the SIM-card for the sake of safety on another memory location and is used if the external apparatus 2 cannot form a connection with a new call number. That ensures that establishing contact always remains possible.

It is also possible to operate a plurality of service centers. The patient reports to any service center. In that way the address of the customer is known there and it is possible to decide which service center initially takes over the procedure. If the customer switches on his external apparatus, then it reports to the preset service center insofar as it immediately sends an SMS-message thereto. Now, by sending back an SMS-message, the service center can transmit the call number which is to be used in future. The mobile portion 3 can thus be automatically associated at any time with another service center without a service engineer having to convert the mobile portion 3. That makes particular sense when it is possible thereby to avoid having to send SMS-messages over frontiers.

The databases of the service centers are the same as each other so that it is always clear which implant 1 or mobile portion 3 is being operated by which service center. Suitable fields are to be provided in the database.

In operation it is possible in each case to pick up only one further (second) number. That is used if the contact with the "new" service center can be successfully achieved. If that is not the case, the "old" call number is used again. If the external apparatus is again referred to a further service center, the second number is overwritten so that the operating procedure involved is always such that firstly the second number is tried and, in the event of one or more abortive attempts, the first number is used. The advantage of this procedure is that it is possible to achieve full flexibility but the secure call number remains stored so that a complete collapse of the connection is reliably avoided.

A kind of LIFO-memory can also be organized in the SIM-card, for a maximum memory depth (for example ten call numbers). If the previously operative service center presets a new call number, that is used as the most up-to-date call number. If however transmission problems occur with that new call number, then in each case the next older call number is used until finally the permanently stored preset call number is next. If the memory is occupied, for example with 9 call numbers and the preset call number, then the oldest, that is to say the call number which is closest to the preset number is erased. The advantage of this procedure is its high level of redundancy as it is to be assumed that a connection occurs with at least one of the stored service centers. The disadvantage is that under some circumstances many service centers receive data from an external apparatus, which only then can be combined together and evaluated jointly.

As the external apparatus 2 is equipped with a modem 12 the call number memory in the SIM-card can additionally also be used for those call numbers. The organization can be implemented based on management of the mobile radio numbers. By virtue of the call numbers being stored on the SIM-card, in the event of replacement of the external apparatus on the part of the customer, for example in the event of a defect, the SIM-card can be fitted into the new apparatus again so that the mode of making the connection to the service centers is implemented without any gap or interruption.

Base Station 4

The base station 4 comprises a charging device 11 for the batteries in the power supply portion 10 and a modem 12, acting as a data transmission device, for the fixed-line telecommunication network 13 which is addressed by the mobile portion 3 by way of the interface device 14. The base station 4 further includes an additional antenna 15 which upon connection to the mobile portion 3 is connected to the mobile radio device 7 and thus improves the transmission quality.

The charging device 11 serves to charge up the Li-ion batteries of the mobile portion 3 and at the same time serves for the power supply for the components of the base station 4. The charging device is equipped with a regulator which is suitable for Li-ion batteries, and a monitoring circuit. It is designed for a maximum charging current of 350 mA. It is dimensionally designed, and can be switched over, for a primary ac voltage of 220/110V, 50/60 Hz, in which respect a range of 100 to 240 V for primary ac voltage and a frequency range of 47–63 Hz is preferred. Protection class "2" is used for the external apparatus 2. The power supply in the base station 4 can also be replaced by a suitable plug mains unit.

The interface device 14 is in the form of an infrared interface (IrDA).

The additional antenna 15 is in the form of a diversity antenna. The arrangement is provided in each case with suitable $\lambda/4$-antennae which are in the form of loop or helix antennae.

There is no mains switch. If the base station 4 is to be disconnected from the mains network, the plug mains unit can be pulled out.

External Apparatus 2: Co-operation of the Mobile Portion 3 and the Base Station 4

The mobile portion 3 is inserted into the base station 4 for the purposes of charging and for data transmission by way of the fixed-line telecommunication network 13.

The base station 4 is equipped with a light-emitting diode which lights up when the mobile portion 3 is plugged in and a charging current is charging the batteries. The light-emitting diode goes out when the mobile portion 3 is removed or current is no longer being taken by the mobile portion 3. The display of the light-emitting diode is inverted for the duration of the transmission, but at least one second, when a message is sent or received by way of the installed modem 12. The base station 4 acknowledges insertion of the mobile portion 3 or removal of the mobile portion 3, by a brief sound from a buzzer.

The mobile portion 3 is fully operational during charging in the base station 4. The voltage transformers in the base station 4 are designed for up to 40 V so that a connection for charging from a motor vehicle system is possible. The control device 5 monitors the battery voltage and the supply of voltage at the mobile radio module 7.1. When the mobile portion 3 is switched on the batteries are fully charged again after about 4 hours in the base station 4.

For the purposes of data transmission the control device 5 is designed in such a way that it is only after a predetermined number of unsuccessful transmission attempts by way of the mobile radio device 7 that the transmission of data to the monitoring device is effected by way of the fixed-line telecommunication network 13 by means of the interface devices 8 and 14 and the modem 12. If therefore the mobile radio transmission is not operating or the external apparatus 2 is being operated in a country which does not support a mobile radio standard, that is to say in the mobile portion 3 there are data which could be put into intermediate storage in the memory of the SIM-card 7.2 and which could not be transmitted by way of the mobile radio network to the service center, then transmission is effected by way of the modem as soon as the mobile portion is plugged into the base station.

The IR-interface 8 of the mobile portion 3 and the IR-interface 14 of the base station 4 are continuously ready to receive. The mobile portion 3 exchanges data with the base station 4 as soon as it is docked thereinto. That means that it is known to the mobile portion 3 in each case whether there is an operational modem 12 in the base station 4.

As the messages to be transmitted involve very short data blocks, a transmission speed of 9600 bauds is sufficient. The modem 12 is either integrated in the base station 4 or if necessary it can be connected by the service engineer by being simply fitted by snapping engagement into the base station 4. The modem 12 can be switched over to a software handshake as it is only that kind of "optical 2-wire transmission" that is supported by way of the IrDA interfaces 8 and 14.

External Apparatus 2: Self-test

If an error is detected in operation, a corresponding inquiry from the service center is received or if the external apparatus 2 goes on the network again after a power-on reset, the external apparatus 2 executes a self-test and signals the result to the service center. The external apparatus 2 therefore automatically signals errors and faults, it can be checked from the service center, and it signals back again when it is again ready for operation (for example after re-charging of the discharged batteries). The SMS-string with the result of the self-test is only transmitted if the foregoing three preconditions require this, no information relating to the self-test is contained in the normal transmission string.

The purpose of the self-test is to permit conclusions to be drawn about the operation of the hardware. A decision can then be taken in the service center how those faults and errors have to be handled. The external apparatus 2 signals in six cases immediately by way of SMS-messages or alternatively by way of a modem:

A dangerous state is being signaled by the pacemaker.

The transmission section to the pacemaker is not operable.

A self-test of the external apparatus signals a fault or error.

Upon signaling of a low battery state prior to power-off.

In the case of a patient alarm, that is to say the patient triggers an alarm by pressing a key of the interface 9.

On demand by the service center.

The following criteria can be adopted as the options in terms of self-diagnosis of the external apparatus:

a) The check sum by way of the program code (flash-ROM, EEPROM, ROMerror, program incorrectly loaded) gave a memory error.

b) A memory test in respect of the RAM gave a memory error.

c) Temporary failure of the mobile radio network has occurred (can also indicate hardware faults; reading out the mobile radio device 7 can clarify matters here).

d) A time-out in communication with the service center has occurred (as c)).

e) A received data string is too short or a check sum error has occurred (hardware fault in the telemetry or reception disturbance or range problems).

External Apparatus 2: Time Synchronization

Only relative time is available for the microprocessors in external apparatuses, with the real-time clock thereof. The time in the implant 1 is not adjusted and after half a year is accurate to +/−0.5 hours so that it cannot be used to establish the system time of the external apparatus 2. If in the mobile portion 3 the battery is discharged or removed by the service engineer, it can happen that the real-time clock totally loses the time. The external apparatus however requires the current time for specifying same in connection with data which are sent to the service center in order to document when events were received from the implant 1.

The data are sent in the form of SMS-messages, and received messages are acknowledged by the service center by way of SMS-messages, in relation to the external apparatus 2. In order to set the current time in the external apparatus 2, that is to say to implement time synchronization of the external apparatus 2, the time signature (SMS-header) of the acknowledgment SMS which contains data and clock time is used.

If that acknowledgment SMS comes back within for example one minute, the external apparatus 2 can set the absolute time in accordance with the header of the acknowledgment, as it is guaranteed that both SMS were on the way for less than a minute. If a longer time has elapsed between the sent SMS and the acknowledgment, the SMS-header of the acknowledgment cannot be evaluated as it is not possible to establish whether the original transmission or the acknowledgment was delayed in transmission. Experience has shown that the time for an SMS-transmission is in the range of below 10 seconds so that the foregoing procedure can be well applied.

As there is a very high probability that, after a power-on reset, the clock time in the external apparatus 2 is wrong, immediate time synchronization is provided for that situation. When the external apparatus 2 connects to the network again after a power-on reset, it signals that to the service center straightaway by way of SMS. The clock of the external apparatus can then be immediately set with the SMS-acknowledgment from the service center.

It is possible to establish that both the service center and also the external apparatus 2 are operated with UTC-time. That means that the entire system operates on one time. Local time such as for example CET or CEST then has to be ascertained from UTC-time when producing doctors' letters.

If problems should arise when ascertaining the absolute time, time transmission by way of the modem 12 can still be used as an alternative. Such a service is generally made available by various providers for the public telephone network.

External Apparatus 2: Service Interface

By way of the interface device 16 for example a service engineer can communicate with the mobile portion 3 using for example a laptop. Another possibility is that the external apparatus operates as a data logger insofar as data (for example as a blood sugar monitor) are read in, which are then also sent to the service center by way of SMS.

The range of the interface device 16 is at least 0.4 m. It is arranged in such a way that it can be used by an apparatus which is beside the external apparatus 2, when the mobile portion 3 is docked into the base station 4. It operates bidirectionally and can transmit data in the half duplex mode. The transmission speed of the third interface device 16 is at least 9600 bauds and can then be stepped up to 115 Kbauds.

The third interface device 16 is to be arranged in such a way that the communication between the base station 4 and the mobile portion 3 operates reliably, that is to say, there is no possibility of influence on the second interface device 8 by the third interface device 16.

FIG. 2 shows a flow chart of a data transmission method which can be used in conjunction with the method according to the invention and which can be used for data transmission between the implant 1 and the external apparatus 2.

The triggering signal for data transmission is in this case always emitted by the transmitter/receiver unit of the implant 1, for which purpose the transmitter/receiver unit is switched on in a step 18.

In step 19 transmission of the first data is then effected from the implant 1 to the external apparatus 2. A string which comprises 17 bytes is transmitted. These are 1 byte synchronization, 4 bytes identification, 1 byte serial number of the transmission, 1 byte length of the string being transmitted, 8 bytes data, and 2 bytes security (CRC). In the case of asynchronous transmission there is an overhead of three bits per byte so that 17*11 bits=187 bits have to be transmitted.

Thereupon step 20 involves plausibility checking of the first data transmitted, by the external apparatus. In that case for example a check is effected in respect of the CRC-bits, in relation to the transmitted string, or a check to ascertain whether the synchronization bits have the previously known values. It is also possible to check whether the string length coincides with the sent string length and/or whether the serial number of the transmission is correct. There is no checking of flags as no handling of the flags takes place in the external apparatus 2. In the event of expansions of the telemetry, the same type of an external apparatus can thus always be used. There is no checking of the implant number as the external apparatus can pass on the information of a plurality of implants.

If the external apparatus in step 20 detects that the data are not plausible, step 22 involves establishing whether a predetermined number of renewed transmission attempts was exceeded.

If it is established in step 22 that the predetermined number of renewed transmission attempts was not exceeded, then in step 23 valid data are again requested from the pacemaker. That request can comprise synchronization (8 bits), identification (32 bits), the serial number of the message (8 bits) and an agreed code (8 bits). That string can also be safeguarded with an CRC-byte. 64 bits+8*3 bits =88 bits are then sent in order to initiate a transmission inquiry in respect of the pacemaker.

If in step 20 the external apparatus detects that the data are plausible, then in step 21, after the plausibility check has been implemented, a first acknowledgment is sent to the implant 1, the first acknowledgment containing a first item of control information for controlling the reception readiness of the first transmitter/receiver unit. If the data set was recognized as being valid, in this case with or in the first acknowledgment a check data set is sent, which is checked by the implant 1. There are two possible options in this respect:

As the safest method, the previously sent first data set is sent back completely to the implant 1 which then compares the sent data set to the received data set. Then 187 bits would be sent back again.

Alternatively synchronization (8 bits), identification (32 bits), the serial number of the transmission (8 bits) and the CRC-bits (16 bits) are sent back for checking purposes to the implant 1 which then checks whether the sent string (identification, number of the transmission) and whether the received CRC-bits conform with the CRC-bits of the sent message. In that case 8 byes are then transmitted instead of 17 bytes as above, that is to say 64 bits+8*3 bits=88 bits (about half in relation to variant 1).

If in step 24 checking of the first acknowledgment in the implant gives a negative result, that is to say if the check data are not identical to the output data, then the first data set is sent again. The implant then tries it again after a fixed period of time. The external apparatus 2 informs the service center about the number of incorrectly transmitted data packets.

If in step 24 checking of the first acknowledgment in the implant gives a positive result, the implant in step 25 sends a second acknowledgment to the external apparatus 2. That second acknowledgment can comprise synchronization (8 bits), identification (32 bits), the serial number of the message (8 bits) and an agreed code (8 bits). That string can also be safeguarded with an CRC-byte. 64 bits+8*3 bits 88 bits are sent.

In step 26 the implant 1 then stops all transmitting and receiving activities.

In step 27 the passing of a given period of time is checked, after which a fresh data set is waiting in the implant to be sent.

After receipt of the second acknowledgment the mobile portion 3 will pass to the service center the first data which have now been verified. The first data set is marked as valid and the service center knows that these data are, with a very high level of probability, correct. The external apparatus retains those first data until the implant supplies a fresh data set which is verified as being correct.

If an error occurs upon reception of the second acknowledgment (for example different implant number or acknowledgment code is not right) the first data are nonetheless sent by SMS to the service center, but in addition the external apparatus 2 signals that the second acknowledgment of the implant 1 could not be validly transmitted.

In this case there is the possibility that the implant 1, after dispatch of the second acknowledgment, after the passing of a precisely fixed period of time, goes into the receive mode again. Upon a renewed inquiry the external apparatus 2 for example can again send the first acknowledgment consisting of 88 bits in order to request a new transmission. Immediately after it has checked that it is addressed the implant 1 can begin with the renewed transmission without the received data first having to be evaluated. In this case the second acknowledgment or the first data set can be sent again. The external apparatus 2 then has in duplicate either the first data set or the second acknowledgment and it can now decide whether the first data set can be assumed to be valid.

The transmission/reception cycles can be repeated a plurality of times. For reasons of saving energy however it is necessary to ensure that the procedure is interrupted after a given number of transmissions in order not to unnecessarily discharge the energy storage means of the implant. The external apparatus should then nonetheless send the data to the service center, but the data must be marked as non-verified. The data are held in the external apparatus 2 until a fresh data set is sent by the implant. In addition the last valid data set should be kept in the external apparatus, which the service center can then interrogate. In the case of a plurality of implants which co-operate with the external apparatus 2, the respectively last data sets of each implant are to be kept in the external apparatus 2.

In the described variant of the method the receiver of the external apparatus 2 is ready at any time to receive data from the implant.

The following point is to be noted in regard to other variants of the method: at regularly recurring or any moments in time, transmissions are sent from the implant 1 to the external apparatus 2, which either contain data or which only indicate that the implant 1 is active and ready to receive. If more than one message is to be sent, they are sent in succession. Those transmissions are received by the external counterpart arrangement, analyzed and acknowledged. The acknowledgments are expected in a fixed time window after transmission so that the receiver in the implant 1 only has to be active for a short time. Data can already be transmitted to the implant 1 in the acknowledgments. On the basis of the content and type of the acknowledgments, this indicates whether further data are waiting in the external apparatus 2 for transmission towards the implant 1. The acknowledgments are respectively analyzed by the implant 1 to ascertain whether the external apparatus 2 wishes to send further data and it will then automatically proceed in the protocol for the transmission of data in the opposite direction (as described above). That cycle can now be repeated as often as may be desired until all data have been transmitted in both directions and no apparatus would want to send further data.

In a further variant, a reduction in energy consumption in the external apparatus 2 is also achieved. As soon as a message has been received from the external apparatus 2, the implant and the external apparatus are synchronized by establishing time segments whereby periodic times are defined, in which the receiver of the external apparatus is active. The implant 1 may then also only transmit within those time segments, if it is to be received. The above-indicated handling instructions are correspondingly modified so that the implant 1 can only send within the time segments and it can no longer send at just any times.

That limitation does not apply for an existing communication (sequence of transmissions and acknowledgments) so that the receiver in the external apparatus 2 still remains active for some time after stopping an acknowledgment in order to be able to receive any consequential transmission that may follow from the implant 1. The implant also must not stop a transmission in any time segment. If the external apparatus 2 is to keep contact with a plurality of implants, then specific time segments are managed for each implant involved, and those time segments as far as possible should not overlap in order to avoid interference in relation to simultaneous transmission in respect of different implants.

The time segments can be altered within the limits of the above-described normal bidirectional communication both in terms of the duration of the active and also the passive phase as well as the time of synchronization. If no further transmissions are received from the implant over a given period of time, then the active time segment is increased in length stepwise at the expense of the passive time segment in order to catch any drift divergence of synchronicity. In the extreme case the receiver in the external apparatus is continuously active. That is also the reset state when switching on.

FIG. 3 in the form of a flow chart shows which strategy can be adopted in the event of repetitions of transmissions by the implant 1. FIG. 3 shows in detail step 22 from FIG. 2 with the input 22.1 and the outputs 22.2 and 22.3.

Step 28 firstly involves checking whether a counter Z has not yet exceeded a predetermined first value, in this case 2. In this respect the counter Z represents the number of transmission attempts executed. In step 18 it is set to zero and it is increased by 1 whenever step 19 is implemented. If the predetermined first value has not yet been exceeded, a new transmission is initiated immediately by way of the output 22.2. Firstly therefore the attempt is made a second time to send the transmission.

If the predetermined first value has been exceeded, then in step 29 a timer is set to zero.

Step 30 then involves checking whether the counter Z has not yet exceeded a predetermined second value, in this case 3. If the predetermined second value has not yet been exceeded, the system waits noticeably by virtue of the waiting loop 31, as a systematic error can be assumed to apply in terms of transmission. That can be for example a disturbing item which makes the transmission impossible for some time (for example a piece of electrical equipment which is not adequately interference-suppressed). After a waiting time of for example 5 minutes, a further transmission attempt is started. If this is also unsuccessful the cycle is continued at step 28.

Step 32 then involves checking whether the counter Z has not yet exceeded a predetermined third value, in this case 4. If the predetermined third value is not yet exceeded the system waits even longer through the waiting loop 33, for example 1 hour, and starts a last transmission attempt. If this is also unsuccessful, the cycle is continued at step 28 and thereafter left at 22.3. In that case therefore transmission is only implemented again when fresh data are ready for transmission in the pacemaker.

FIG. 4 shows a block circuit diagram of a variant of a patient monitoring system using the present invention.

In this case data transmission takes place between the implant 1 and the external apparatus shown in FIG. 1, the implant 1 being worn by a patient 33. From the external apparatus 2, the read-out data are transmitted by way of a mobile radio section 34 of a mobile radio network to a mobile radio station 35 of the mobile radio network and from there sent also by way of a mobile radio section 36 or alternatively by way of a fixed-line network connection 37 to a service center 38 which serves as a central storage arrangement and monitoring arrangement. In this case all data are sent in the form of SMS-messages and mutually acknowledged by way of SMS.

The service center, or, for example, a central storage unit, 38 is provided with a fully automatic database. The medical data are automatically read by way of TCP/IP-connection into the database computer where they are respectively entered into the provided tables and table fields, in respect of moment in time, implant, patient, external apparatus and medical contact (doctor/clinic).

Upon the attainment of a certain degree of filling of the database, the data are transferred from the computer onto external media (for example CD or tape). In accordance with the medical guidelines for data security patient-related data are stored immediately (as far as may be possible) on external read only media (CD-ROM). Proper access to all externally safeguarded data is continuously possible by way of suitable references in the database.

The access options to the data are regulated by complex rights allocation (for example reading, writing, modifying, erasing, etc.) for various user groups such as data managers, clinic or doctor. During operation of the database manual interventions and inquiries by system operators and other clients (for example the doctor 40) are possible at any time.

Priority-controlled triggers in the database and a coupled expert system make it possible to react specifically to medical facts and situations: the database generates in accordance with predefined rules items of information for the doctor and the system operator and passes such information to the target apparatuses 39 by way of fax, e-mail and internal and external computer connections. The items of information which are outputted are kept for later collective inquiry in the database. In that way the doctor can again request a summarizing or lost report in relation to the patient. He receives medical information in a few minutes even during examination and summarized information relating to the next after-care date. The transmission medium and the target addresses can in this case be configured independently of the triggering time and event. In that way the attending doctor 40 can obtain information about the state of health of his patient 33, in a manner as is wanted by the doctor.

In an emergency the patient 33 can thus also receive medical help more quickly than usual. That emergency situation is triggered both by objectively measured medical data and also by depressing a key on the mobile portion 3. He enjoys highest priority, in relation to the other events.

In addition the database can also react separately to data transmissions which are triggered by the patient, for example insofar as in this case also information is sent to the doctor and the system operator. In that way the subjective condition of the patient can be taken into account to a particular degree in the data acquisition procedure, and also incorporated into the diagnosis options.

FIG. 5 shows a block circuit diagram of a variant of a patient monitoring and after-care system using the present invention.

In this case the patient 33 with the implant 1 and the external apparatus 2 for after-care investigation are disposed in the interrogation region 41 of an after-care arrangement. In this case, triggered by the triggering device 42 which co-operates with the external apparatus upon entering the interrogation region 41, interrogation of the first data from the implant 1 is automatically executed by the doctor 40 prior to the after-care examination. In this case transmission of the first data is effected by means of the long-range telemetry connection between the implant 1 and the external apparatus 2.

The result of the interrogation passes in suitably processed form by way of the path described in relation to FIG. 4 by way of the service center 38 to the target apparatus 39 from which it is outputted to the doctor 40 for his information. At the same time further patient-related data are also outputted from the database of the service center 38 so that the doctor 40 can form a comprehensive picture.

The routine current investigation by the doctor is thus supplemented by an overall picture over the time since the last visit to the doctor. The doctor acquires a picture over a number of weeks or months, which is substantially more informative than the current examination. In this case, a good picture is formed of the lifestyle habits of the patient, whereas it is precisely the appointment with the doctor that can represent an exceptional situation from the usual lifestyle (travel to the clinic or to the doctor, going up stairs, stress in traffic etc.).

In the actual examination the doctor (for example in carrying out stress tests) can also immediately request a report from the service center 38, which is then supplied after a few minutes. In that way parameter changes which were set by means of the programmer can be immediately checked and possibly also optimized. Further reports can be produced by virtue of storage in the database and further evaluation options by the expert system or by comparison with other cases. In that way, due to advances in medical knowledge, it is possible to recognize new correlations. They are then notified to the doctor in the next report, without the doctor having to check each of his patients for possible effects and consequences, when fresh knowledge comes to light.

In a further variant of the invention it is additionally possible, as soon as the patient 33 enters the interrogation region 41 of an after-care arrangement, to automatically start given standard test or diagnosis programs which are normally only carried out under medical supervision. It is possible for example to implement stimulus threshold, sensitivity, stress or defibrillation-shock tests.

FIG. 6 shows a variant of the invention from FIG. 5 in which an external apparatus 2' is fixedly installed in the interrogation region 41 of the after-care arrangement. In this case the interrogation procedure is triggered as soon as the patient 33 with the implant 1 is in the interrogation range of the external apparatus 2' for a certain period of time.

The result of the interrogation procedure goes in suitably processed form directly from the external apparatus 2' to the target apparatus 39 from which it is outputted to the doctor 40 for his information. At the same time further patient-related data are also acquired by way of the connection 43 from the database of the service center 38 and outputted at the target apparatus 39 so that in this case also the doctor 40 can have a comprehensive picture.

FIG. 7 shows a block circuit diagram of a telemetry device of an electromedical implant which can be used together with the present invention.

The telemetry device has a close-range transmitter 44, a telemetry unit 45 connect ted thereto and an antenna interface device 46 which is connected to the telemetry unit 45 and by way of which a close-range antenna 47 is connected to the close-range transmitter/receiver unit.

In addition, to form a long-range telemetry device, the arrangement has a long-range transmitter 48 connected to the telemetry unit 45 and a long-range antenna 49 connected to the antenna interface device 46.

Furthermore the close-range telemetry device and the long-range telemetry device have separate energy storage means 51 and 52.

The other necessary system components for a telemetry device such as intermediate storage means, operational control, encoding, decoding and driver with threshold detector are in this case integrated in the telemetry unit 45.

For switching over between the long-range transmitter 48 and the close-range transmitter 44, they are connected to the telemetry unit 45 by way of a switching unit 46.1. For switching over between the close-range antenna 47 and the long-range antenna 49, they are connected to the antenna interface device 46 by way of a further switching unit 46.2. I t will be appreciated however that in other variants, the two transmitters, like also the two antennae, can also be disposed connected in parallel to the telemetry unit 45 and the antenna interface unit 46 as in general close-range and long-range telemetry are not operated simultaneously.

To provide for adaptation of the modulation method for the respective telemetry involved, the arrangement has a matching logic unit 50 which is connected to the telemetry unit 45. The long-range telemetry device is operated at substantially the same effective data rate as the close-range telemetry device.

FIG. 8 shows the transmitter/receiver unit 53 of an embodiment of the implant 1, in which separate energy storage means 56 and 57 are provided for the transmitter 54 and the receiver 55. The energy storage means involve separate buffer capacitors 56 and 57. These capacitors 56 and 57 only have to be charged to the level of energy necessary for the respective procedure. The energy consumption of the one procedure does not influence the energy supply for the other procedure. The procedures can thus directly follow each other, which is advantageous in relation to a bidirectional communication protocol without charging of a single buffer capacitor to double the energy content being necessary for that purpose.

FIG. 9 shows a circuit diagram of a transmitter according to the invention of the first transmitter/receiver unit of a variant of the implant from FIG. 1.

In this case a stable, frequency-modulatable transmitter has been embodied by means of two bipolar transistors 58, 59, wherein the first transistor 58 in a Colpitts or Clapp circuit with an SAW-resonator 60 forms an SAW-stabilized oscillator, and the second transistor 59 serves as a buffer stage and antenna driver. The transistors 58, 59 are designed for maximum gain at lowest collector current. The frequency can be modulated by a capacitance diode 61 in series with the SAWresonator 60. The frequency variation and thus the data rate and/or the range of the transmitter can however be increased the capacitance diode being replaced by a PIN-diode which is switched by a further transistor.

The antenna used can be a simple wire loop or an open wire (throw-out antenna) in the contour of the header of the implant. Overall in this case at 400 MHz a current consumption of less than 1 mA is possible, at a range of several meters.

The circuit can be supplied directly from a buffer capacitor fed by a high-resistance battery of the implant 1, or from a low-resistance battery. There is no need for a charge pump.

FIG. 10 shows a further embodiment of an apparatus according to the invention which substantially corresponds to that shown in FIG. 1, for which reason reference will only be made here to the differences involved.

This arrangement involves an external apparatus 2" which is suitable for monitoring, actuating and transmitting data from various electronic apparatuses 1'. Uses can be the remote monitoring of installations, for example the degree of filling of automatic drinks dispensers or automatic vending machines, a link with domestic technology, for example the control and monitoring of the air conditioning installation or the heating system, coupling to alarm installations or glass breakage signaling installations, for example burglary signaling by way of mobile radio, coupling to measurement systems, for example weather stations and level metering units on rivers, coupling to systems for traffic observation and control, for example traffic signs, bridges etc. It can also be used as a bugging system or as a mobile telephone with special digital functions.

The differences in relation to the structure shown in FIG. 1 essentially concern the mobile portion: 3' of the external apparatus 2". In this case the first interface device includes four potential-free inputs 6.1 by way of optocouplers and four potential-free outputs 6.2. By virtue of the potential separation of the inputs and outputs 6.1 and 6.2, the external apparatus 2" is suitable for monitoring and controlling digital states.

In addition the receiving and-transmitting portion 16 of FIG. 1 is not included here, instead the serial interface 63 (RS 232) which is thus liberated is taken out by way of a 9-pole plug. In the case of the RS232 a software handshake with three lines (RXD, TXD, GND) is sufficient. That means that the transmission rate is also limited to 9600 bauds. The serial interface 63 is not designed to be potential-free. By way of a further plug 64 the connections of the mobile radio module 7.1 can be taken to a microphone, a loudspeaker and optionally a buzzer (6 lines) so that for further areas of use it is possible to add a listening/speech combination and a buzzer.

The inputs 6.1 are in the range 1 at between –3V and 1.5V L-level, between 3.5 and 8V H-level and 10 mA input current; while in the range 2 they are at between –3V and 8V L-level, between 18V and 30V H-level and 10 mA input current. State recognition is implemented by way of an LED-display at a maximum switching frequency of 100 Hz rectangular and a separation voltage of 2.5 kV.

The outputs have between 15 and 30V DC separate voltage feed, a load current of 200 mA, short-circuit protection, protection from thermal overloading and a separation voltage of 2.5 kV. Potential separation is effected by way of optocouplers and the power switching function by way of MOS-FETs.

A difference in relation to the structure shown in FIG. 1, in respect of the base station 4', only arises in regard to the power supply by the plug mains unit 11', instead of the mains unit in the base station. A further possible configuration provides that the base station is omitted and the external apparatus is supplied directly by way of a mains unit. In the event of mains failure the mobile portion then still continues to operate for about 20 hours.

The invention is not limited in terms of implementation thereof to the preferred embodiments set forth hereinbefore. On the contrary a large number of alternative configurations are possible, which make use of the illustrated structure even in configurations of a basically different kind.

What is claimed is:

1. An electromedical implant having devices for data exchange with an external apparatus, which include a close-range antenna and a close-range transmitter/receiver unit with a close-range transmitter, a telemetry unit and an antenna interface device which is connected to the telemetry unit and by way of which the close-range antenna is connected to the close-range transmitter/receiver unit, characterized in that there is provided a long-range transmitter connected to the telemetry unit to provide a long-range telemetry device.

2. An implant as set forth in claim 1 characterized in that there is provided at least one long-range antenna connected to the antenna interface device.

3. An implant as set forth in claim 2 characterized in that for switching over between close-range and long-range telemetry the close-range antenna and the long range antenna are connected to the antenna interface device by way of a switching unit.

4. An implant as set forth in claim 1 characterized in that there is provided a matching logic unit connected to the telemetry unit for adaptation of the modulation method for the respective telemetry involved.

5. An implant as set forth in claim 1 characterized in that the long-range telemetry device is designed for operation at substantially the same effective data rate as the close-range telemetry device.

6. An implant as set forth in claim 1 characterized in that there is provided a separate energy supply for the long-range telemetry device and the close-range telemetry device.

7. An electromedical implant for close-range and long-range data exchange with an external apparatus, comprising:
   a telemetry unit;
   a close-range transmitter/receiver unit with a close-range transmitter;
   a long-range transmitter/receiver unit with a long-range transmitter;
   a close-range antenna;
   a long-range antenna; and
   an antenna interface device connected to the telemetry unit, the antenna interface device connecting the close-range antenna to the close-range transmitter/receiver unit, the antenna interface device also connecting the long-range antenna to the long-range transmitter/receiver unit.

8. An implant as set forth in claim 7, wherein the close-range antenna and the long-range antenna are connected in parallel circuits with each other.

9. An implant as set forth in claim 7, wherein the close range transmitter and the long-range transmitter are connected in parallel circuits with each other.

10. An implant as set forth in claim 7, further comprising a switching unit connected to the close-range antenna and the long-range antenna for switching over between close-range and long-range telemetry.

11. An implant as set forth in claim 7, further comprising a switching unit connected to the close-range transmitter and the long-range transmitter for switching over between close-range and long-range telemetry.

12. An implant as set forth in claim 7, further comprising a matching logic unit connected to the telemetry unit for adaptation of the modulation method for the respective telemetry involved.

13. An implant as set forth in claim 7, having long-range telemetry and close-range telemetry operating at substantially the same effective data rate.

14. An implant as set forth in claim 7, further comprising separate energy supplies for long-range telemetry and close-range telemetry.

15. A patient monitoring system with close-range and long-range telemetry, comprising:

an electrical implant; and an external apparatus comprising a mobile portion and a base station;

the electrical implant comprising a first telemetry unit, a close-range transmitter/receiver unit with a close-range transmitter, a long-range transmitter/receiver unit with a long-range transmitter, a close-range antenna, a long-range antenna, and an antenna interface device connected to the telemetry unit, the antenna interface device connecting the close-range antenna to the close-range transmitter/receiver unit, the antenna interface device also connecting the long-range antenna to the long-range transmitter/receiver unit; and the mobile portion having a control device, a first interface device to contact the implant and a second interface device to connect with the base station.

16. A system of claim 15, wherein the mobile portion is configured modularly, wherein one module includes a transmitting/receiving antenna and an actuating system, and another module includes a further interface device for connection to a mobile telephone.

17. A system of claim 16, wherein any of the first interface device, the second interface device and the further interface device is an infrared interface.

18. A system of claim 15, wherein the mobile portion further comprises a mobile radio device.

19. A system of claim 18, wherein the base station includes an additional antenna adapted for connection to the mobile radio device.

20. A system of claim 15, wherein the electrical implant further comprises a switching unit connected to the close-range antenna and the long-range antenna for switching over between close-range and long-range telemetry.

21. A system of claim 15, further comprising a central storage unit to store data transmitted from the external apparatus.

22. A system of claim 21, further comprising a mobile radio station to transmit data from the external apparatus to the central storage unit.

23. A system of claim 21, further comprising at least one target apparatus to receive data from the central storage unit.

24. A system of claim 15, wherein the implant and external apparatus are disposed in an interrogation region.

25. A system of claim 24, further comprising a triggering device responsive to said external apparatus upon entering the interrogation region.

26. A system of claim 15, wherein the external apparatus is fixedly installed in an interrogation region.

* * * * *